(12) United States Patent
Reich et al.

(10) Patent No.: US 9,975,941 B2
(45) Date of Patent: May 22, 2018

(54) METHOD FOR PURIFYING TERIPARATIDE (71) Applicant: RICHTER-HELM BIO TEC GMBH & CO. KG, Hamburg (DE)

(72) Inventors: Christoph Reich, Heide (DE); Michael Kuechler, Hamburg (DE)

(73) Assignee: RICHTER-HELM BIO TEC GMBH & CO. KG, Hamburg (DE)

( * ) Notice: Subject to any disclaimer, the term of this patent is extended or adjusted under 35 U.S.C. 154(b) by 128 days.

(21) Appl. No.: 14/938,758

(22) Filed: Nov. 11, 2015

(65) Prior Publication Data
US 2017/0129935 A1    May 11, 2017

(51) Int. Cl.
*C07K 14/635* (2006.01)
*C07K 1/18* (2006.01)
*B01D 15/36* (2006.01)
*B01D 15/16* (2006.01)

(52) U.S. Cl.
CPC .......... *C07K 14/635* (2013.01); *B01D 15/168* (2013.01); *B01D 15/362* (2013.01); *C07K 1/18* (2013.01)

(58) Field of Classification Search
None
See application file for complete search history.

(56) References Cited

U.S. PATENT DOCUMENTS

| | | |
|---|---|---|
| 4,105,602 A | 8/1978 | Colescott et al. |
| 4,427,827 A | 1/1984 | Stevenson |

FOREIGN PATENT DOCUMENTS

| | | | | |
|---|---|---|---|---|
| EP | 2905289 | 8/2015 | | |
| WO | WO 2009019715 | * | 2/2009 | ........... C07K 14/635 |

OTHER PUBLICATIONS

Andersson et al., Large-scale synthesis of peptides, Biopolymers, 55(3):227-250 (2000).
Mant et al., *HPLC Analysis and Purification of Peptides*, Methods in Molecular Biology, New York: Marcel Dekker, 386, 3-55 (2007).
Merrifield, Solid phase peptide synthesis. I. The synthesis of a tetrapeptide, J. Am. Chem. Soc., 85(14):2149-54 (1963).
Suzuki et al., High-level production of recombinant human parathyroid hormone 1-34, Appl. Env. Microbiol., 62(2):526-9 (1998).
Yamamoto, et al., *Ion-Exchange Chromatography of Proteins*, Chromatographic Science Series, vol. 43, New York: Marcel Dekker (1988).

* cited by examiner

*Primary Examiner* — Anand Desai
(74) *Attorney, Agent, or Firm* — Marshall, Gerstein & Borun LLP (57) ABSTRACT

The present invention relates to a novel method for purifying teriparatide, a therapeutically active polypeptide fragment of full-length human parathyroid hormone. The method is based on ion exchange chromatography and is effective in separating the therapeutically active polypeptide from undesirable variants, such as truncated polypeptides. The method of the invention can be used at a preparative scale which allows it to be implemented into the production process for teriparatide. Accordingly, the invention also provides a method for the production of teriparatide which includes a step in which teriparatide is purified by the novel ion exchange chromatography method of the invention.

17 Claims, 4 Drawing Sheets a b

METHOD FOR PURIFYING TERIPARATIDE

The present invention relates to a novel method for purifying teriparatide, a therapeutically active polypeptide fragment of full-length human parathyroid hormone. The method is based on ion exchange chromatography and is effective in separating the therapeutically active polypeptide from undesirable variants, such as truncated polypeptides. The method of the invention can be used at a preparative scale which allows it to be implemented into the production process for teriparatide. Accordingly, the invention also provides a method for the production of teriparatide which includes a step in which teriparatide is purified by the novel ion exchange chromatography method of the invention.

BACKGROUND OF THE INVENTION

Parathyroid hormone (PTH) is a polypeptide hormone which is naturally produced in the parathyroid of mammals. The human polypeptide consists of 84 amino acids and is involved in the regulation of the calcium concentration in blood plasma. If the calcium level drops below a threshold level, PTH is secreted by cells of the parathyroid glands into the blood and induces a release of calcium from bone tissue. At the same time, PTH supports calcium absorption from the small intestine and enhances calcium reabsorption from the primary urine, thereby suppressing calcium loss via the kidneys. Due to its calcium releasing effects, an excessive amount of PTH in the blood as commonly observed in primary and secondary hyperparathyroidism has been found to be associated with reduced bone density and bone atrophy (osteoporosis). Considering the physiological effects of PTH, it appears odd that the hormone nevertheless proved useful in the therapy of osteoporosis.

However, animal studies in rats for the first time revealed that a short-term exposure to PTH supports bone formation due to transient activation of osteoclasts, whereas a sustained exposure ultimately results in bone atrophy. Subsequent clinical studies in humans using the pharmaceutically active fragment PTH1-34 of human PTH confirmed that the fragment can be used for treating osteoporosis. PTH1-34 is a polypeptide having a molecular mass of 4.7 kDa that consists of the first 34 amino acids of the human PTH hormone. It was approved for osteoporosis therapy in 2002 under the product name "teriparatide". Teriparatide is sold by Lilly Pharma under the trade name Forteo (in the US) and Forsteo (in Europe).

At present, PTH1-34 for therapeutic use is produced by heterologous expression in bacterial host cells and subsequent purification of the pharmacological active polypeptide. However, it has been found that all known fragments and variants of PTH1-34 occur during the production process demonstrate a reduced potency compared to PTH1-34. In addition a negative effect on overall purity is observed. For example, a number of fragments derived from PTH1-34 were identified in the final batch obtained after heterologous expression, including amongst others PTH1-30, PTH2-34, PTH3-34 and PTH4-34. Moreover, chemical modifications of certain amino acids of PTH1-34, e.g. oxidation of methionine residues or deamidation of asparagine residues, give rise to additional variants.

However, as homogeneity of a product intended to be used as a therapeutic is of utmost importance for safety reasons, any kind of truncated or chemically modified form of PTH1-34 in the final product is clearly undesirable. Accordingly, current production processes normally include one or more chromatography steps that aim at the purification of the PTH1-34 polypeptide. However, it has been found to be problematic to separate PTH1-34 from some of its variants and fragments without significant product loss. In particular, it was observed that the fragment PTH2-34 shows essentially the same retention properties in ion exchange chromatography as PTH1-34. Consequently, the PTH2-34 fragment is co-eluted with PTH1-34 which makes PTH1-34 purification challenging. Moreover, alternative chromatographic techniques, e.g. reversed phase chromatography, were tested but did not show any potential for a preparative separation of truncated and full-length teriparatide.

In light of the above, new methods are needed which are effective in separating PTH1-34 from its fragments and chemically modified variants. The method of the present invention provides for the effective purification of the PTH1-34 polypeptide by cation exchange chromatography using inversely directed gradients of pH and ionic strength. As discussed in more detail below, the method is particularly suitable for separating PTH1-34 from PTH2-34.

BRIEF DESCRIPTION OF THE FIGURES

FIG. 1a shows the amino acid sequence and the distribution of charges in PTH1-34. FIG. 1b shows the secondary structure of PTH1-34.

DETAILED DESCRIPTION OF THE INVENTION

The present invention is based on the surprising insight that teriparatide (also referred to herein as PTH1-34) can be effectively purified in an ion exchange chromatography process by increasing the pH and simultaneously decreasing the ionic strength in the fluid used for eluting the polypeptide from the cation exchange material. The use of such inversely directed gradients has not been disclosed in the prior art. Instead, it was basic knowledge in the field of ion exchange chromatography that polypeptides, which have bound to an ion exchanger, can be eluted by increasing the ionic strength in the eluent, e.g., by increasing the salt concentration in the eluent (S. Yamamoto, K. Nakanishi, R. Matsuno (1988), "Ion-Exchange Chromatography of Proteins", Chromatographic Science Series, Vol. 43, Marcel Dekker, New York; C. T. Mant et al. (2007), "HPLC Analysis and Purification of Peptides", Methods in Molecular Biology, Vol. 386, 3-55). Decreasing the ionic strength in the eluent is not a usual step in ion exchange chromatography. It is therefore surprising that a dual gradient as applied in the method of the present invention is suitable for providing highly purified PTH1-34.

In a first aspect, the present invention therefore relates to a method for purifying PTH1-34 by ion exchange chromatography, said method comprising the steps of:

(a) contacting a fluid containing PTH1-34 with a cation exchange material under conditions that allow for the reversible binding of PTH1-34 to said cation exchange material;

(b) optionally washing the cation exchange material to remove unbound material;

(c) eluting PTH1-34 by increasing the pH and decreasing the ionic strength.

PTH1-34 and Impurities Derived Thereof

The present method has been found to be effective for purifying therapeutically active PTH1-34 which is present in a fluid from any undesired PTH1-34 variants and fragments which might also be present in said fluid. These fragments may include, for example, truncated forms of PTH1-34 which can be regarded as product related impurities resulting from the polypeptide production process. For example, the most common way of producing PTH1-34 includes heterologous expression of the polypeptide in *E. coli* host cells. It was found that heterologous expression of PTH1-34 may give rise to N-terminally and C-terminally truncated forms of PTH1-34 which are unacceptable and have to be removed from the product for safety reasons.

In particular, it has been observed that PTH2-34, a truncated form of PTH1-34 which lacks the N-terminal serine residue, is regularly present after heterologous expression. The overall amount of the truncated PTH2-34 in the product solution obtained is up to 1% (w/w). Other possible truncated forms of PTH1-34 might lack the first 2 or 3 amino acids at the N-terminus. These variants are referred to herein as PTH3-34 and PTH4-34, respectively. In a preferred embodiment of the invention, the ion exchange chromatography method provided herein is applied for the purpose of removing one or more of the N-terminally truncated fragments PTH2-34, PTH3-34 and PTH4-34. In a particular preferred embodiment, the claimed method is directed to the removal of the truncated fragment PTH2-34.

Apart from N-terminally truncated fragments of PTH1-34, the fluid to be subjected to the purification method of the present invention may also contain C-terminally truncated forms of PTH1-34. For example, fragments which lack 1, 2, 3 or 4 of the amino acids located at the C-terminus in PTH1-34 may occur. Therefore, in another preferred embodiment, the ion exchange chromatography method provided herein is applied for the purpose of removing one or more of the C-terminally truncated polypeptides PTH1-33, PTH1-32, PTH1-31 and PTH1-30. In a particularly preferred embodiment, the claimed method is applied for removing PTH1-30.

In a still further embodiment of the present invention, the new method is carried out for the purpose of removing chemically modified variants of PTH1-34 comprising modifications at one or more amino acid side chains. These variants may arise as product related impurities in the production of PTH1-34. A number of variants of PTH1-34 have been identified which differ from the original polypeptide in that certain amino acid residues have been oxidized, deaminated and/or modified by succinimide formation. For example, a variant has been identified which has a deaminated asparagine residue in position 16 of PTH1-34. Another variant has oxidized methionine residues in position 8 and/or 18 of PTH1-34. Like with the truncated fragments, it is required for safety reasons to remove these variants from the final PTH1-34 product.

Figure 1:
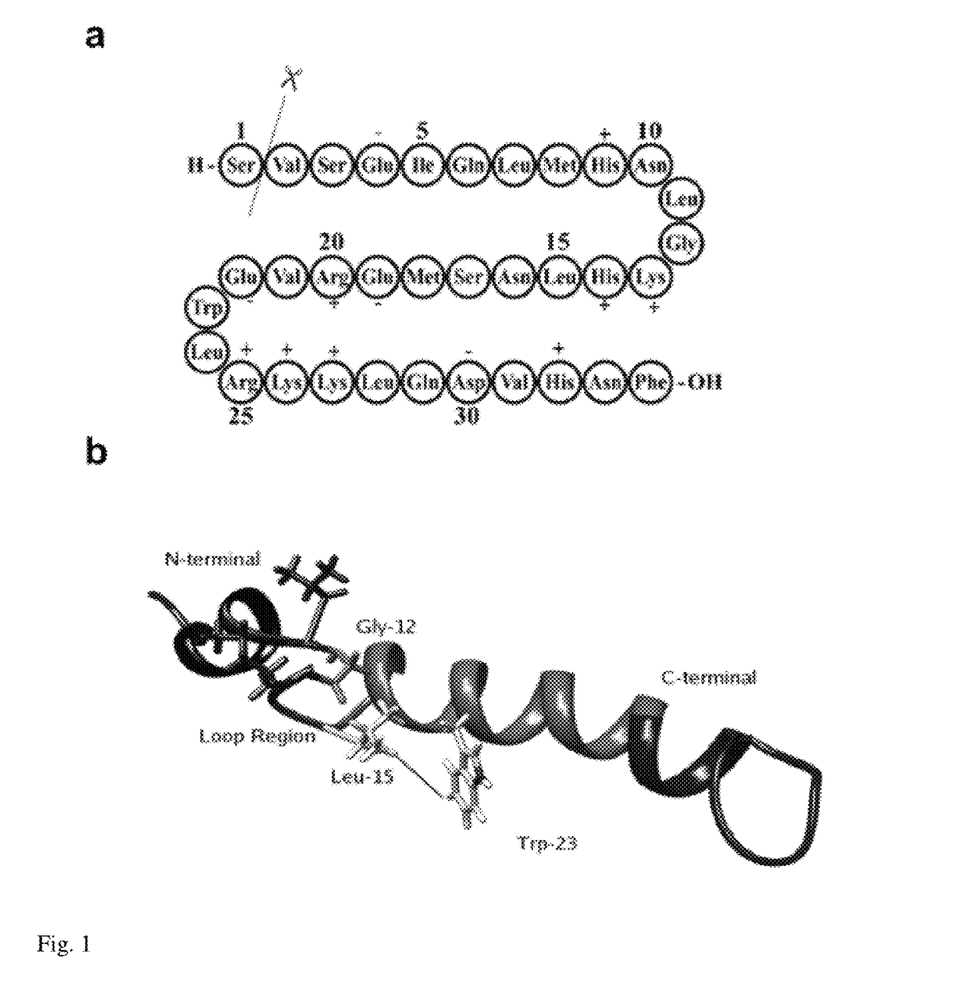
FIG. 1 shows the primary and secondary structure of the parathyroid hormone fragment PTH1-34.

The PTH1-34 to be purified with the method of the invention preferably comprises or consists of the amino acid sequence set forth in SEQ ID NO:1. The polypeptide depicted in SEQ ID NO:1 corresponds to the 34 N-terminal amino acids of the naturally occurring human parathyroid hormone. For comparison, the amino acid sequence of the full-length human parathyroid hormone is shown in SEQ ID NO:2. FIG. 1a shows the distribution of the charged amino acids within the PTH1-34 sequence of SEQ ID NO:1. Under physiological conditions, the PTH1-34 sequence of SEQ ID NO:1 comprises two alpha-helical regions that are connected via a loop region (see FIG. 1b). No tertiary structure had been observed for the molecule under physiological conditions.

Also encompassed by the term "PTH1-34" are homologs of the sequence set forth in SEQ ID NO:1. As used herein, homologs of the PTH1-34 of SEQ ID NO:1 are polypeptides which differ from the polypeptide in SEQ ID NO:1 in a limited number of amino acids, e.g. in 1, 2, 3, 4, 5, 6, 7, 8, 9, 10, 11, 12 or more amino acids. Preferably, the homolog differs in no more than 15 amino acid from the polypeptide depicted in SEQ ID NO:1. For example, the polypeptide to be purified by the method of the invention can be a polypeptide which differs from PTH1-34 as shown in SEQ ID NO:1 in that no more than 1, 2, 3, 4, or 5 amino acids have been substituted by other amino acids. Where an amino acid substitution is made, the substitution preferably is a conservative amino acid substitution, i.e. a substitution of one amino acid by another amino acid of similar polarity which can act as a functional equivalent. Preferably, the amino acid used as a substitute is selected from the same group as the amino acid residue to be substituted. For example, a hydrophobic residue can be substituted with another hydrophobic residue, or a polar residue can be substituted with another polar residue having the same charge. Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

It is particularly preferred that the PTH1-34 homolog which may comprise 1, 2, 3, 4, or 5 amino acid substitutions compared with the PTH1-34 of SEQ ID NO:1 comprises no chemical modifications, such as oxidations, deamidations, cyclizations, and the like. It is furthermore preferred that the homolog comprises or consists of 34 amino acids.

According to the invention, the PTH1-34 polypeptide which is to be subjected to the method of the invention can be derived from any suitable method which is known in the art for producing polypeptides. The polypeptide may have been prepared both by ribosomal and non-ribosomal methods. For example, the PTH1-34 may have been chemically synthesized by solid phase or liquid phase methods. Protocols for solution-phase chemical synthesis of peptides have been described (see, e.g., Andersson et al., Biopolymers 55:227-250, 2000). For solid phase synthesis the basic technique described by Merrifield (J. Am. Chem. Soc., 1964, 85, 2149-2154) may have been used. In that approach, the growing peptide is anchored on an insoluble resin, and unreacted soluble reagents are removed by filtration or washing steps without manipulative losses. The solid phase synthesis technique of Merrifield has been improved in the last decade and nowadays allows the synthesis of polypeptides with up to 50 amino acids. The chemical synthesis of PTH1-34 fragments was disclosed, e.g. in the U.S. Pat. No. 4,427,827 and U.S. Pat. No. 4,105,602.

Alternatively, the PTH1-34 polypeptide to be purified according to the invention can be a recombinantly produced PTH1-34, i.e. the polypeptide has been produced by biotechnological processes that involve genetically modified cells or organisms. Typically, a nucleotide sequence encoding the PTH1-34 polypeptide is cloned into a suitable vector which provides for the expression or overexpression of the polypeptide in a host cell. The vector is introduced into a prokaryotic or eukaryotic host cell, and the cell is cultured under conditions suitable for the expression of the polypeptide. Normally, the polypeptide to be expressed will be under the control of an inducible promoter so that expression may be initiated by the addition of an inducer, e.g. IPTG, to the culture medium. After incubation of the cells to allow expression, the cells are usually harvested and homogenized to release the recombinant PTH1-34 polypeptide. Finally, the polypeptide is recovered by one or more purification steps. In accordance with the present invention, it is particularly preferred that the PTH1-34 polypeptide is a polypeptide that has been recombinantly produced by heterologous expression in host cells.

To simplify its subsequent enrichment and purification, the recombinant PTH1-34 may be prepared in form of a fusion polypeptide. As used herein, a fusion polypeptide refers to a fusion of the amino acid sequence of PTH1-34 to a second amino acid sequence. The second amino acid sequence may be, for example, an affinity tag, i.e. an amino acid sequence which is either N-terminally or C-terminally fused to the PTH1-34 polypeptide, and which has a strong affinity to another compound or material, thereby allowing enrichment and/or purification of the fusion polypeptide as a whole. The affinity tag may be, for example, a poly-histidine sequence comprising 6-12 histidines which specifically interact with a nickel ion chelate matrix or alternative IMAC resins. Alternatively, the affinity tag may be a glutathione-S-transferase which allows the purification via a glutathione matrix. Further affinity tags are well-known in the art. An affinity tag sequence can be removed from the PTH1-34 sequence after purification with the affinity matrix, for example, by providing a proteolytic cleavage site between PTH1-34 and the affinity tag.

The recombinant PTH1-34 may be expressed in high amounts in the bacterial host cells so that inclusion bodies are formed in which the recombinant polypeptides are present in partially folded form and aggregate through non-covalent hydrophobic or ionic interactions. Where the method for producing the recombinant PTH1-34 provides the polypeptide in inclusion bodies, it will preferably also include a step in which the polypeptides in the inclusion bodies are solubilised and refolded. Methods for solubilisation and refolding of polypeptides from inclusion bodies are well known in the art.

Chromatographic Device and Cation Exchange Material

The present method is preferably carried out by use of a FPLC (fast protein liquid chromatography) device, i.e. an automated device which comprises a column which includes the cation exchange material as the stationary phase, one or more pumps which provide a pressure that is sufficient for causing the mobile phase (i.e. the buffers used for binding, washing and elution) to flow through the cation exchange material, an apparatus which collects the fractions eluted from the column, and a detector that is capable of detecting the PTH1-34 which is eluted from the column. Detection can be achieved by measuring the absorption at a wavelength of e.g. 280 nm. In addition, the changes in pH and conductivity can also be monitored in the fractions. A considerable number of automated FPLC devices which are suitable for cation exchange chromatography are commercially available from different manufacturers. Non-limiting examples for such chromatographic devices include the ÄKTApurifier, ÄKTAavant, ÄKTApilot, ÄKTAexplorer or ÄKTAprocess systems (GE Healthcare, the K-Prime 40 systems (Merck Millipore), the NCG systems (Bio-Rad), and similar devices. The use of these automated devices is, however, not mandatory for carrying out the method of the present invention.

The method of the invention can make use of any cation exchange material that has been described in the art as being useful for the purification of polypeptides. As used herein, the cation exchange material is an insoluble polymeric matrix which comprises on its surface negatively charged functional groups that are capable of attracting cations or positively charged molecules. The cation exchange material can be in the form of porous beads having, e.g., a size of between 10-100 µm, preferably 20-80 µm. A number of different cation exchange materials are known in the art, including cross-linked natural polymers, organic polymers and inorganic materials. While carboxymethyl groups are commonly used in weak cation exchangers, strong cation exchangers often include sulfopropyl groups. When performing the method of the present invention, it is preferred that the cation exchanger is present in the form of a packed column suitable for use in an automated FPLC device, such as the Äkta Purifier 100 FPLC System.

In another preferred embodiment of the invention the cation exchange material used in the purification method is a strong cation exchanger which comprises sulfoethyl, sulfopropyl, sulfobutyl and/or sulfoisobutyl as functional groups. Cation exchanger materials which comprise a mixture of one or more of the above groups may likewise be used in the method of the invention. Further, the cation exchange material can be based on any common polymeric material which has been described for use in this particular type of chromatography. For example, the polymeric cation exchange material can comprise cross-linked polystyrene divinylbenzene, polymethacrylate, styrene-divinylbenzene, cross-linked Agarose, silica-based matrices, polyvinyl ether, cellulose, and dextran.

Cation exchange materials or columns containing these materials can be purchased from different providers and include, e.g. the Unosphere S 70 resin (Biorad, Munich, Germany), the Nuvia™ S resin (Biorad, Munich, Germany), the Poros HS20 or HS50 resin (Life Technologies, Darmstadt, Germany), the Source 15S or 30S resin (GE Healthcare, Freiburg, Germany), the Polysulphoethyl A resin (PolyLC, Columbia, USA), the Ceramic HyperD F(S) resin (Pall, Dreieich, Deutschland), the Bakerbond™ PolyCSX35 Bioseparation Media (Avantor Performance Materials, Center Valley, USA), the Eshmuno S and CPX resins (Merck Millipore, Darmstadt, Germany), the Toyopearl resins SP-650M and GigaCap S-650M (Tosoh Bioscience LLC, King of Prussia, USA) and other cation exchange stationary phases regularly used for purifying proteins.

The use of one of the following resins is particularly preferred in the method of the invention: the Eshmuno S resin, the Eshmuno CPX resin, the Poros HS20 resin, and the Toyopearl GigaCap S-650M resin. A further particularly preferred cation exchange resin material for use in the method of the invention is the Fractogel® resin developed by Merck Millipore. The Fractogel® resin uses the so-called "tentacle technology" which means that the surface of the resin beads comprises long polymer chains which provide for an improved accessibility of the proteins to be purified to the functional groups of the resin material. The method of the invention is preferably carried out with the Fractogel® resin EMD SE Hicap (M), the Fractogel® resin EMD $SO_3^-$ (S), or the Fractogel® resin EMD $SO_3^-$ (M). Use of the Fractogel® resin EMD $SO_3^-$ (S) is particularly preferred according to the invention.

The cation exchange columns used in the purification method disclosed herein can be of any size. Given that the method of the invention aims at the purification of PTH1-34 from production batches, the use of preparative columns which allow for the binding of high amounts of PTH1-34 is particularly preferred. Preparative columns having a bed volume of 1-100 L can be used, whereas bed volumes of 10-50 L are particularly preferred, for example 45 L. For example, the preparative columns used in the purification method of the present invention can have a bed volume of at least 1 L, at least 2 L, at least 3 L, at least 4 L, at least 5 L, at least 10 L, at least 20 L, at least 25 L, or more. Usually, preparative columns useful in the method of the invention will have a diameter of between 1-100 cm, whereas a diameter of between 20-80 cm, or 40-60 cm is particularly preferred.

Analytical columns having bed volumes of 1-5 mL may be used for further optimizing the conditions of the cation exchange purification method of the invention, for example, to adjust the method to other polypeptides. It should, however, be noted that conditions that were found highly useful for an analytical column might not equally be transferable to the conditions on a preparative column (see Examples below).

Sample and Column Preparation

The method of the invention uses as a starting material a fluid that contains PTH1-34. The fluid can be the supernatant of a cell culture that was used for heterologous expression of the polypeptide. For example, it is possible to subject the supernatant comprising the soluble PTH1-34 polypeptides and other soluble components of the host cells directly to the ion exchange chromatography method of the invention, either with or without prior dilution. It is, however, preferred that before applying the purification method of the invention the supernatant obtained from cell culture is further processed, e.g. by centrifugation, filtration, size-exclusion chromatography, affinity chromatography, RP-HPLC, and the like, to remove undesired substances, e.g. polynucleotides and/or polysaccharides, to cleave off an affinity tag or another peptide or polypeptide that is fused to PTH1-34, and/or to enrich the PTH1-34 polypeptide. The fluid to be used in the method of the inventiom preferably comprises the PTH1-34 polypeptide in substantially enriched form which means that at least 50% of the polypeptide compounds dissolved in the fluid is PTH1-34.

In one embodiment, the fluid used as a starting material in the method of the invention is obtained from a prior reversed phase chromatography run, i.e. the fluid is the eluate of reversed phase chromatography. This eluate will contain significant amounts of organic solvents, such as acetonitrile, and it might be necessary to dilute it with a suitable buffer before applying it to the cation exchange material. Conveniently, the buffer used for dilution can be the same buffer that was used for equilibrating the cation exchange material. The eluate from the reversed phase chromatography can be diluted by factor 1, 2, 3, 4, 5, 6, 7, 8, 9, 10 or more. A dilution by factor 2-4 has been proven particularly useful. Where dilution is not possible, e.g., due to an excessive amount of acetonitrile in the fluid, a complete buffer exchange may be performed, which means that PTH1-34 is transferred from the reversed phase eluate to a buffer that is adjusted to subsequent ion exchange chromatography. A buffer exchange can be easily accomplished, e.g. by tangential flow filtration, size exclusion chromatography, diafiltration or dialysis. It is preferred that PTH1-34 is transferred to the buffer which is used during binding of the polypeptide to the cation exchange material (referred to in the following as "binding buffer").

Before application of the fluid containing the PTH1-34 polypeptide to the cation exchange material, the cation exchange material will usually be equilibrated by washing the column with 1-50, preferably 1-25, and more preferably 1-10 column volumes of an equilibration buffer to provide conditions that promote binding of the polypeptide to the cation exchanger. Preferably the equilibration buffer and the binding buffer are identical. After equilibration, the fluid containing the PTH1-34 polypeptide is contacted with the cation exchange material.

Contacting PTH1-34 with the Cation Exchange Material

According to step (a) of the above method, the fluid containing PTH1-34 is contacted with the cation exchange material under conditions that provide for the binding of the polypeptide to the polymeric matrix of the cation exchanger. This means that the conditions in terms of temperature, pressure and pH are such that PTH1-34 can displace the cations that have bound to the cation exchange material after equilibration. In particular, the binding of the polypeptide to the cation exchange material is facilitated by selection of an appropriate pH of the binding buffer.

For identifying a suitable pH that allows binding of the PTH1-34 to a particular cation exchange material, the polypeptide can be contacted with the cation exchanger of choice under different pH conditions while detecting the amount of the polypeptide in the flow-through. In this way, a suitable pH range for binding of the polypeptide to the cation exchanger can be readily determined. It is preferred according to the invention that the pH is selected such that the PTH1-34 is present in the form of a positively charged polypeptide which supports its binding to the cation exchanger. To provide positively charged PTH1-34 polypeptide molecules the pH of the buffer used in the binding step should preferably be below the isoelectric point of the polypeptide. The PTH1-34 set forth in SEQ ID NO:1 has an isoelectric point of 8.3. Thus, where it is intended to purify the PTH1-34 of SEQ ID NO:1 with the method of the present invention, the pH in the binding step should be selected to be below 8.3.

Preferably, the binding buffer used for application of the PTH1-34 polypeptide of SEQ ID NO:1 to the cation exchange material will be adjusted to a pH of 8.0 or less. It will be particularly preferred that the pH of the binding buffer will be at least 0.5 pH units, more preferably at least 1.0, at least 1.5, or at least 2.0 pH units below the isoelectric point of the polypeptide to be purified. Where the method of the invention is performed with the PTH1-34 set forth in SEQ ID NO:1, binding of the polypeptide to the cation exchange material is preferably performed in binding buffer having a pH below 7.8, below 7.3, below 6.8, and more preferably below 6.3, or even below 6.0. For example, the PTH1-34 of SEQ ID NO:1 is bound to the cation exchange material using binding buffer at a pH of between 6.0 and 8.0, preferably at a pH of between 6.5 and 7.5, and more preferably at a pH of between 6.8 and 7.2. In cases where a homolog of PTH1-34 is used which differs from the PTH1-34 in SEQ ID NO:1 by 1, 2 or 3 amino acid substitutions, it may be possible that the isoelectric point of said modified polypeptide is slightly different. The skilled person will be readily able to determine the isoelectric point of the homolog by use of routine methods well known in the art.

The present invention is amongst others based on the insight that chromatographic separation of PTH1-34 from its fragments and variants can be improved by eluting PTH1-34 from the cation exchange material by increasing the pH and simultaneously lowering ionic strength in the mobile phase. This can be conveniently be accomplished by using an eluent which, compared to the binding or washing buffer, has a higher pH and a lower conductivity. Thus, the binding buffer used for binding PTH1-34 to the cation exchange resin in the method of the invention will exhibit an ionic strength which is higher than that of the eluent. This is unusual for cation exchange chromatography, because the ionic strength in the eluent is normally gradually increased to support displacement of polypeptides from a cation exchanger. The conductivity (as expressed in mS/cm) of the buffers used in the ion exchange chromatography process is a suitable measure that reflects ionic strength of said buffer. Accordingly, the terms "conductivity" and "ionic strength" are used interchangeably herein.

It is preferred that the binding buffer has a conductivity that is at least 30% higher, at least 50% higher, at least 75% higher, at least 100% higher, at least 150% higher, at least 200% higher, or at least 300% higher than the conductivity of the corresponding eluent. The conductivity of the binding buffer will preferably be in the range 1.5-3.0 mS/cm, for example, more than 1.5 mS/cm, more than 1.6 mS/cm, more than 1.7 mS/cm, more than 1.8 mS/cm, more than 1.9 mS/cm, more than 2.0 mS/cm, more than 2.1 mS/cm, more than 2.2 mS/cm, more than 2.3 mS/cm, more than 2.4 mS/cm, more than 2.5 mS/cm, more than 2.6 mS/cm, more than 2.7 mS/cm, more than 2.8 mS/cm, or more than 2.9 mS/cm. Preferably, the conductivity of the binding buffer will be at least 0.5 mS/cm higher than the conductivity of the corresponding eluent, more preferably at least 0.6 mS/cm, at least 0.7 mS/cm, at least 0.8 mS/cm, at least 0.9 mS/cm, at least 1.0 mS/cm, at least 1.1 mS/cm, at least 1.2 mS/cm, at least 1.3 mS/cm, at least 1.4 mS/cm, at least 1.5 mS/cm, at least 1.6 mS/cm, at least 1.7 mS/cm, at least 1.8 mS/cm, at least 1.9 mS/cm, or at least 2.0 mS/cm.

In a preferred aspect, the conductivity of the binding buffer is in the range between 2.0 and 3.0 mS/cm, and the conductivity of the eluent is in the range between 0.5 and 1.5 mS/cm. In an even more preferred aspect, the conductivity of the binding buffer is in the range between 2.5 and 2.8 mS/cm, and the conductivity of the eluent is in the range between 1.0 and 1.3 mS/cm.

Several buffers can be used in the method of the present invention. It is preferred according to the invention that the binding buffer and the elution buffer are prepared with the same buffer substance. The buffer compound used for preparing the binding buffer and the elution buffer is selected such that its pH range covers the isoelectric point of the PTH1-34 polypeptide, i.e. the $pK_a$ value of the buffer substance is not more than one pH unit higher or lower than the isoelectric point of the PTH1-34 polypeptide. Where the PTH1-34 polypeptide to be purified is the polypeptide of SEQ ID NO:1, the buffer will be selected such that its pH range covers pH 8.3, i.e. the buffering compound has a $pK_a$ of between 7.3 and 9.3. A pH range in the area of the isoelectric point of the PTH1-34 has the particular advantage that the preparation of the binding buffer, which preferably has a pH of below 7.5, and more preferably a pH around 6.5, will require considerable amounts of acid, such as HCl, for pH adjustment. The addition of HCl or other acids to the binding buffer will increase the ionic strength of the binding buffer relative to the elution buffer, the latter of which has a higher pH and therefore requires only slight or no pH adjustment.

Suitable buffer substances having a $pK_a$ in the range of 8.3 include Tris(hydroxymethyl)aminomethane (referred to as "Tris" herein), triethanolamine, and borate buffer. Additional buffers that have been found to be suitable for carrying out the method of the invention include a barbital buffer having a pH in the range of, e.g., 6.8-9.2, and a glycylglycine buffer having a pH in the range of, e.g., 7.3-9.3. The use of Tris buffer is preferred herein, because it was unexpectedly found to result in a particularly good separation of PTH1-34. The use of Tris buffer was not an obvious measure in the method of the invention, because Tris is commonly recommended in the literature for use in anion exchange chromatography. Tris is a cationic buffer which is in principle able to bind to the functional groups of the cation exchange resin, thereby disturbing reproducible separation. In the method of the present invention, however, it was observed that the use of Tris does not negatively influence the purification of PTH1-34 via cation exchange chromatography.

The buffering compound will be present in the binding buffer in an amount of 1-200 mM, preferably 10-100 mM, and more preferably 20-80 mM. Where Tris is used in the binding buffer, the preferred concentration will be in range of 20-40 mM, wherein 20 mM is particularly preferred. Additional salts, such as NaCl or $KH_2PO_4$, may be used as additives in amounts of 1-100 mM, preferably 20-80 mM, to adjust the conductivity of the buffer where necessary. Other buffering compounds, such as Bis-Tris may also be added to the Tris buffer. Non-limiting examples for a Tris-based binding buffer which is suitable to be used in the purification of the PTH1-34 polypeptide of SEQ ID NO:1 include:

20 mM Tris, pH 6.5-7.5
30 mM Tris, pH 6.5-7.5
40 mM Tris, pH 6.5-7.5
20 mM Tris, 20 mM $KH_2PO_4$, pH 6.5-7.5
30 mM Tris, 30 mM $KH_2PO_4$, pH 6.5-7.5
40 mM Tris, 40 mM $KH_2PO_4$, pH 6.5-7.5
20 mM Tris, 20 mM Bis-Tris, pH 6.5-7.5
30 mM Tris, 30 mM Bis-Tris, pH 6.5-7.5
40 mM Tris, 40 mM Bis-Tris, pH 6.5-7.5

Based on his experience and the information and the particular examples provided herein, the skilled person will be readily able to prepare additional binding buffers that are suitable for being used in the purification process of the present invention.

The contacting of the PTH1-34 polypeptide with the cation exchange material can be performed in different ways, depending on the particular equipment which is used for carrying out the method of the invention. Where an FPLC device is used for the purification process of the invention, the PTH1-34 polypeptide can be contacted with the cation exchange material conveniently by injecting the PTH1-34 containing fluid (either diluted with binding buffer or not) into an injection loop which is then introduced into the flow of the binding buffer. The flow rate during binding will be in the range of 50-400 cm/h, preferably 100-300 cm/h, more preferably 150-200 cm/h.

When using preparative columns having a having a bed volume size of 1-50 L, the PTH1-34 will be applied to the column such that the overall protein load is in the range of 2.0-4.5 g/L. In approaches using columns having a bed volume size of 10-250 mL, the overall protein load is in the range of 10-20 mg/mL. When using analytical columns having a bed volume size of less than 10 mL, e.g., 5 mL or 1 mL, the overall protein load will normally be in the range of 0.1-5 mg/mL, e.g. about 1 mg/mL.

Washing the Cation Exchange Resin

After protein binding the cation exchange material is optionally washed to remove unbound material. For this purpose, the cation exchange material is preferably washed with several column volumes of washing buffer. According to the invention, the washing buffer may be identical to the binding buffer in terms of its pH or ionic strength. The washing buffer may contain additional compounds not included in the binding buffer. In any case, however, the pH and ionic strength of the washing buffer should be adjusted to avoid any premature elution of the PTH1-34 polypeptide from the cation exchange material.

Depending on the size of the column used in the method of the invention, it will be useful to wash the column after polypeptide binding with 1-25 column volumes, preferably 1-15 column volumes, and more preferably 1-10 column volumes. In an even more preferable embodiment of the invention, the cation exchange resin is washed after PTH1-34 binding until the detected UV absorption, pH and conductivity signals remain constant.

Eluting the PTH1-34 Polypeptide

After PTH1-34 binding to the cation exchange material and (where applicable) washing said material, the PTH1-34 polypeptide is eluted. According to the invention, elution is effected by increasing the pH and decreasing the ionic strength. Compared with the binding buffer, the eluent will thus have a higher pH which is close to the isoelectric point of the PTH1-34 polypeptide. By increasing the pH, the overall positive charge of the PTH1-34 polypeptide is reduced and the polypeptide will ultimately be released from the cation exchange material. Preferably, the eluent is an elution buffer, i.e. it comprises at least one buffering compound.

The increase in pH can be accomplished in different ways. For example, a gradient elution can be conducted in which the eluent is gradually mixed with the binding or washing buffer. In this way, the pH of the mobile phase flowing over the cation exchange material gradually increases so that different polypeptides, which have bound to the cation exchange material, are released in accordance with their interaction strength. The gradient used can be a convex, concave or linear gradient, but linear gradients are particularly preferred. The steepness of the gradient can be varied as needed. Normally, linear gradients with a steepness of 1-5% elution buffer per column volume are useful for carrying out the method of the invention. Alternatively, an isocratic stepwise elution can be performed by switching from binding or wash buffer directly to 100% eluent without any gradient. In an isocratic stepwise elution, the composition of the eluent remains constant during elution, because the eluent is not gradually mixed with binding or washing buffer in the course of elution.

The eluent used for releasing the PTH1-34 polypeptide from the cation exchange material will be adjusted to a pH of 8.0 or higher. It will be preferred that the pH of the eluent will be 0.1 pH units, 0.2 pH units, or 0.3 pH units higher or lower than the isoelectric point of the PTH1-34 polypeptide to be purified. Where the method of the invention is performed with the PTH1-34 of SEQ ID NO:1, the eluent preferably has a pH of at least 8.0 or more, at least 8.1 or more, at least 8.2 or more, at least 8.3 or more, at least 8.4 or more, at least 8.5 or more, or at least 9.0 or more. In cases where a homolog of PTH1-34 is used which differs from the PTH1-34 in SEQ ID NO:1 by 1, 2 or 3 amino acid substitutions, it may be possible that the isoelectric point of said modified polypeptide is slightly different. Therefore, the optimum pH to be used during the elution step might slightly vary from that determined for the PTH1-34 of SEQ ID NO:1.

As stated above in the context with the binding buffer, the eluent used for elution of PTH1-34 will have an ionic strength which is significantly lower than that of the binding and/or washing buffer. Preferably, the eluent will have a conductivity in the range 0.1-1.4 mS/cm, for example, less than 1.4 mS/cm, less than 1.3 mS/cm, less than 1.2 mS/cm, less than 1.1 mS/cm, less than 1.0 mS/cm, less than 0.9 mS/cm, less than 0.8 mS/cm, less than 0.7 mS/cm, less than 0.6 mS/cm, less than 0.5 mS/cm, less than 0.4 mS/cm, less than 0.3 mS/cm, or less than 0.2 mS/cm. In another aspect, the conductivity of the eluent is in the range between 0.2 and 1.4 mS/cm, preferably between 0.5 and 1.3 mS/cm.

The buffer used for preparing the eluent will preferably be the same as the one used for binding and/or washing buffer, wherein Tris, triethanolamine, and borate buffer are preferred for use. The use of Tris buffer is particularly preferred.

The buffering substance will be present in the eluent in an amount of 1-200 mM, preferably 10-100 mM, and more preferably 20-80 mM. Where Tris is used in the eluent, the preferred concentration will be in range of 20-40 mM. An amount of 20 mM Tris in the eluent is particularly preferred. Additional salts, such as NaCl or $KH_2PO_4$, may be used as additives in amounts of 1-100 mM, preferably 20-80 mM. Other buffering compounds, such as Bis-Tris may also be added to the Tris buffer. Non-limiting examples for a Tris-based eluent which is suitable to be used in the purification of the PTH1-34 polypeptide of SEQ ID NO:1 include:

20 mM Tris, pH 9.0
30 mM Tris, pH 9.0
40 mM Tris, pH 9.0
20 mM Tris, 3 mM $KH_2PO_4$, 13 mM $K_2HPO_4$, pH 9.0
30 mM Tris, 4 mM $KH_2PO_4$, 14 mM $K_2HPO_4$, pH 9.0
40 mM Tris, 5 mM $KH_2PO_4$, 15 mM $K_2HPO_4$, pH 9.0
20 mM Tris, 20 mM Bis-Tris, 5 mM KCl, pH 8.2
20 mM Tris, 20 mM Bis-Tris, 5 mM KCl, pH 8.3
20 mM Tris, 20 mM Bis-Tris, 5 mM KCl, pH 9.0
20 mM Tris, 20 mM Bis-Tris, 5 mM KCl, pH 10.0

The elution will be performed by applying 10-50 column volumes to the cation exchange material. If a linear gradient from 0-100% eluent is used, the gradient may be applied in 10-50 column volumes. Gradient volumes of 10-20 column volumes are expected to provide the best compromise between peak dilution and resolution.

Preferred Modes for Carrying Out the Purification

The purification method of the invention is able to separate therapeutically active PTH1-34 from chemically modified by-products and fragments. It is preferred that the eluate obtained in step (c) contains less than 5% impurities, i.e. proteinaceous compounds which are not unmodified PTH1-34. Specifically, it is preferred that the eluate obtained in step (c) contains less than 5% (w/w) of the PTH2-34 fragment and/or less than 5% deaminated PTH1-34. Even more preferably, the eluate obtained in step (c) contains less than 0.5%

(w/w) of the PTH2-34 fragment and/or less than 0.5% deaminated PTH1-34. In a most preferred embodiment of the method, the eluate obtained in step (c) contains no detectable PTH2-34.

According to a particularly preferred embodiment of the invention, the PTH1-34 to be purified is the polypeptide depicted in SEQ ID NO:1, and the purification method is performed with a buffer system comprising eluent A: 20 mM Tris (with or without 20 mM Bis-Tris), pH 6.5-7.0, and eluent B: 20 mM Tris (with or without 20 mM Bis-Tris), pH 8.0-10.0. It is moreover preferred to initiate elution by performing a stepwise elution with 75-100% eluent B.

According to the invention, it is possible to add further compounds to eluent A or B that may prove advantageous for a number of embodiments of the invention. For example, the elution buffer may comprise 250 mM sucrose, Tween 20 (1%), urea (1-2 M) and/or arginine (50-100 mM).

Preparation of the PTH1-34 Polypeptide

The purification method described above can be part of a process for the preparation of PTH1-34. This means that the purification method of the present invention can be implemented into a manufacturing process which includes the heterologous expression of the polypeptide and several downstream processing steps which are directed to the refolding and purification of the polypeptide.

Thus, in another aspect, the present invention also relates to a method for preparing PTH1-34, in particular the PTH1-34 of SEQ ID NO:1, comprising the steps of (a) recombinantly expressing PTH1-34 in a host cell;

(b) optionally disrupting the host cells to release the recombinantly expressed PTH1-34;

(c) purifying the PTH1-34 by a purification method as described in more detail above.

In step (a) of the above manufacturing method, the PTH1-34, or a homolog thereof as described elsewhere herein, is recombinantly expressed in a host cell, such as a prokaryotic or eukaryotic host cell. In a preferred embodiment of the manufacturing method of the invention, the PTH1-34 is expressed in bacterial host cells, e.g. in bacteria of the genus *Escherichia*. The manufacturing method may use, for example, common bacterial strains of *E. coli* for expression of high amounts of the PTH1-34 polypeptide.

After expression of the polypeptide in the cells, it may be necessary to disrupt the cells to release the recombinant polypeptide from the cytoplasm. Alternatively, where the polypeptide is secreted by the host strain in the supernatant, e.g. as a result of the use of appropriate signal peptides, it will not be necessary to disrupt the cells. Instead, the recombinant polypeptide can be directly obtained from the culture supernatant. The recombinant polypeptide can be further processed, e.g. by removal of the signal peptide.

In step (c) of the above manufacturing method, the PTH1-34 is purified by employing the cation exchange chromatography method referred to above.

Preferably, the method for preparing PTH1-34 also comprises one or more additional chromatography steps, such as reversed phase chromatography, which are performed prior to or subsequent to step (c).

EXAMPLES

Example 1: Purification of PTH1-34 on an Analytical Column

The conditions for separating PTH1-34 from the N-terminally truncated PTH2-34 were analyzed on an analytic Fractogel $SO_3^-$ (S) cation exchange column with a volume of 1 mL (diameter 0.8 mm, height: 20 mm). Eluate from a reversed phase chromatography containing approximately 0.6 mg/mL PTH1-34 was applied to the column at a load of approximately 1 mg/mL of the resin.

Binding of the polypeptides to the column was performed in Eluent A (also used as binding buffer) consisting of 20 mM $KH_2PO_4$, pH 6.5. Elution was performed by use of Eluent B consisting of 20 mM $KH_2PO_4$, 500 mM KCl, pH 6.5. The eluent was applied in a linear gradient of 0-100% eluent in 60 column volumes. The flow rate was 120 cm/h. Fractions of 1 mL were collected. For each of the collected samples, the extinction at 220 nm was measured.

Figure 2:
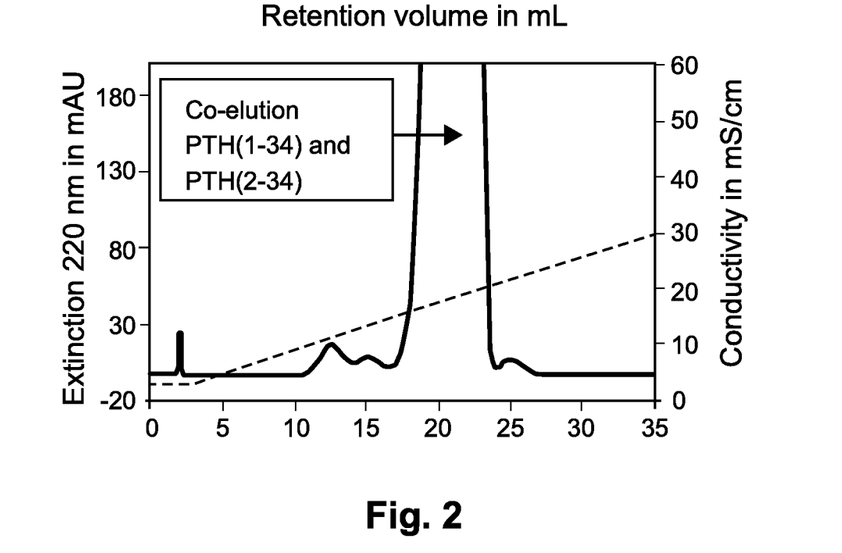
FIG. 2 shows the attempt to separate PTH1-34 from PTH2-34 by cation exchange chromatography at analytical scale using a salt gradient. Column volume (CV): 1 mL. Resin: Fractogel $SO_3^-$ (S). Eluent A: 20 mM $KH_2PO_4$, pH 6.5. Eluent B: 20 mM $KH_2PO_4$, 500 mM KCl, pH 6.5. Loading: 1 mg/mL resin. Gradient 0-100% eluent B in 60 CV. Flow rate: 120 cm/h.

The result of the chromatography is depicted in FIG. 2. It can be seen that PTH1-34 and PTH2-34 co-eluted in the same peak. It was evidently not possible under the conditions applied to separate PTH1-34 and PTH2-34 to a sufficient extent. There was no binding selectivity of either PTH1-34 or PTH2-34 to the Fractogel $SO_3^-$ (S) cation exchange column. Accordingly, efforts were made to provide an improved method for purifying PTH1-34 and obtaining increased yields.

Example 2: Purification of PTH1-34 on a 29 ml Column

To define robust and reliable scale up conditions, a number of different conditions were tested using a Fractogel $SO_3^-$ (S) cation exchange column with a volume of 29 mL. Improvements were observed when using an increasing pH instead of an increasing salt concentration for elution. To provide for a low ionic strength during elution, the buffers were prepared such that eluent A (which corresponds to the binding buffer) has a high ionic strength and eluent B has a significantly lower ionic strength. Tris buffer was found to be particularly useful for this approach. The following conditions were tested:

| Process run | Buffer Conditions | Gradient [% B/CV] | Loading [mg/cm² and mg/mL Resin] | Step Yield [%] |
|---|---|---|---|---|
| P225 | Eluent A: 20 mM Tris 20 mM Bis-Tris pH 6.5 Cond. 2.7 mS/cm Eluent B: 20 mM Tris 20 mM Bis Tris 5 mM KCl pH 10.0 Cond. 0.8 mS/cm | 2.7 (40% wash; 40-100% elution) | 60/6 | 76 |
| P226 | Eluent A: 20 mM Tris 20 mM Bis-Tris pH 6.5 Cond. 2.7 mS/cm Eluent B: 20 mM Tris 20 mM | 2.5 (45% wash; 45-100% elution) | 65/4.5 | 73 |

-continued

| Process run | Buffer Conditions | Gradient [% B/CV] | Loading [mg/cm² and mg/mL Resin] | Step Yield [%] |
|---|---|---|---|---|
| P242 | Bis Tris 5 mM KCl pH 10.0 Cond. 0.8 mS/cm Eluent A: 20 mM Tris 20 mM Bis-Tris pH 6.5 Cond. 2.7 mS/cm Eluent B: 20 mM Tris 20 mM Bis Tris 5 mM KCl pH 10.0 Cond. 0.8 mS/cm | (0% wash; 75% elution) | 65/4.5 | 92 |
| P243 | Eluent A: 20 mM Tris 20 mM Bis-Tris pH 6.5 Cond. 2.7 mS/cm Eluent B: 20 mM Tris 20 mM Bis Tris 4 mM KCl pH 8.3 Cond. 1.3 mS/cm | (0% wash; 100% elution) | 65/4.5 | 88 |
| P250 | Eluent A: 20 mM Tris 20 mM Bis-Tris pH 6.5 Cond. 2.7 mS/cm Eluent B: 20 mM Tris 20 mM Bis Tris 4 mM KCl pH 8.2 Cond. 1.4 mS/cm | (0% wash; 100% elution) | 65/4.5 | 75 |
| P251 | Eluent A: 20 mM Tris 20 mM Bis-Tris pH 6.5 Cond. 2.7 mS/cm Eluent B: 20 mM Tris 20 mM Bis Tris 4 mM KCl pH 8.1 Cond. 1.3 mS/cm | (0% wash; 100% elution) | 65/4.5 | 75 |

Eluate from a reversed phase RP chromatography containing approximately 0.6 mg/mL PTH1-34 was diluted by factor 2 to reduce the acetonitrile content. The RP eluate was applied to the column at loads of 4.5-6 mg/mL resin. The column was washed with 3 column volumes binding buffer (eluent A). Elution from the resin was effected either with isocratic elution or gradient elution.

Fractions of 10 mL were collected. For each of the collected samples, the extinction at 220 nm was measured.

Figure 3:
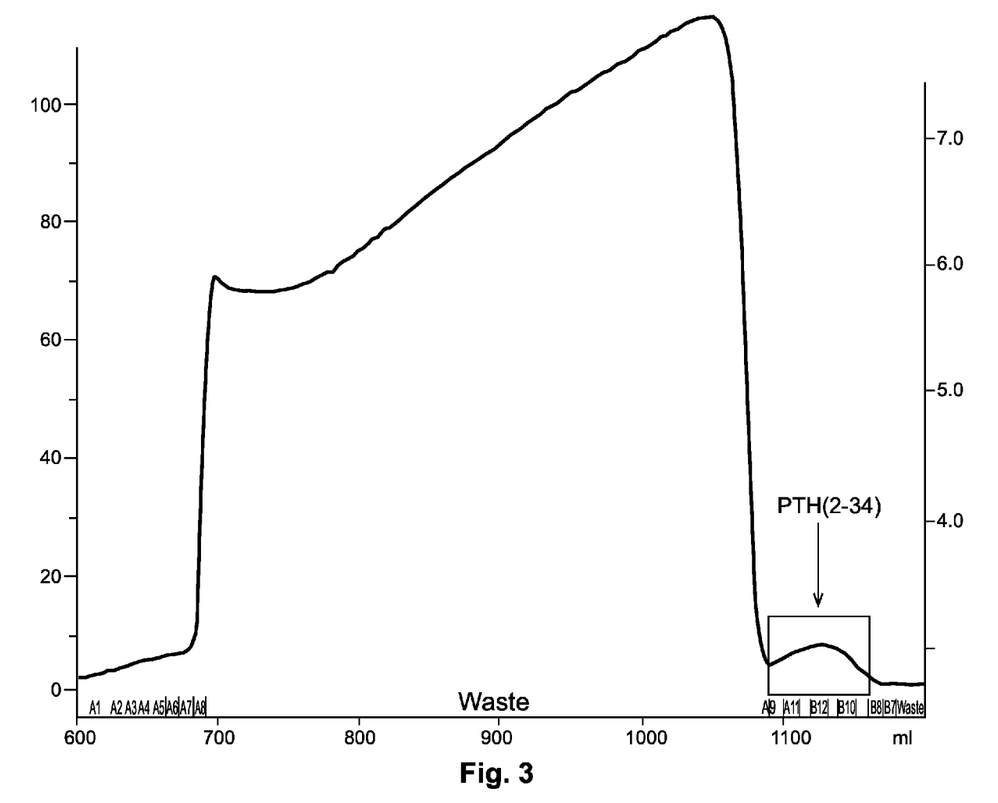
FIG. 3 shows the chromatographic separation of PTH1-34 and PTH2-34 using a cation exchange column with a column volume of 29 mL. Eluent A: 20 mM Tris, 20 mM Bis-Tris, pH 6.5. Eluent B: 20 mM Tris, 20 mM Bis-Tris, 4 mM KCl, pH 8.2. Loading: 4.5 mg/mL resin. Stepwise elution with 13.5 column volumes of 100% elution buffer. Resin: Fractogel $SO_3^-$ (S). Flow rate: 150 cm/h.

As can be seen from the above table, PTH1-34 yield was significantly increased by elution using a pH increase/ionic strength decrease. FIG. 3 exemplarily shows the result of process run P250. It can be seen that the modified elution profile has the effect that PTH2-34 is eluted as a separate peak which allows for its separation from the PTH1-34 product.

Example 3: Purification of PTH1-34 on a 26.3 L Column

The method of the invention was tested at preparative scale using a Fractogel $SO_3^-$ (S) cation exchange column having a volume of 26.3 L (column diameter: 450 mm, column height 166 mm). The PTH1-34 preparation used in this chromatographic step was recombinantly expressed PTH1-34 that had previously been subjected to reversed-phase (RP) chromatography. The PTH1-34 preparation obtained from the RP chromatography step contained approximately 1.2% PTH2-34.

To reduce the acetonitrile concentration, the main fraction obtained from RP chromatography was diluted 1:2 with Eluent A (20 mM Tris, 20 mM potassium dihydrogen phosphate, pH 6.5, conductivity about 4.1 mS/cm) and loaded onto the column. The column was washed with an initial gradient ranging from 0-35% Eluent B (20 mM Tris, 16 mM dipotassium hydrogen phosphate, 4 mM potassium dihydrogen phosphate, pH 8.9, conductivity about 3.5 mS/cm) in one column volume and, in a subsequent step, at 35% Eluent B for 10 column volumes. The flow rate was adjusted to 100 cm/h. The column was loaded with 3.5 g/L of the polypeptide. Elution was performed with a gradient from 35-100% Eluent B in 22 column volumes.

Figure 4:
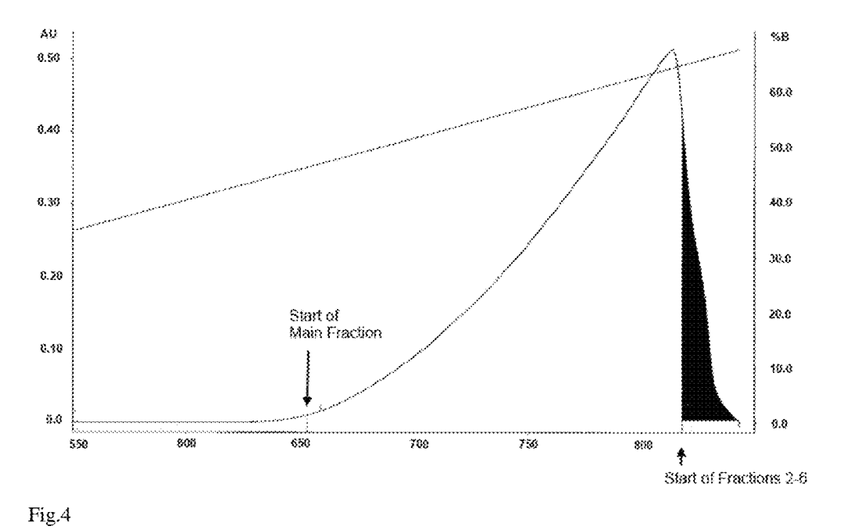
FIG. 4 shows the chromatographic separation of PTH1-34 and PTH2-34 at preparative scale using a cation exchange column with a column volume of 26.3 L. Eluent A: 20 mM Tris, 20 mM potassium dihydrogen phosphate, pH 6.5. Eluent B: 20 mM Tris, 16 mM dipotassium hydrogen phosphate, 4 mM potassium dihydrogen phosphate, pH 8.9. Loading: 3.5 g/L resin. Resin: Fractogel $SO_3^-$ (S). Flow rate: 100 cm/h.

The PTH1-34 product was found to elute in the slowly ascending peak shown in FIG. 4, while PTH2-34 eluted in the steeply descending peak area (i.e., the area shown in black in FIG. 4). Fractions of the peak were collected for subsequent analysis by ultra high performance liquid chromatography (RP-uHPLC). A first fraction ("fraction 1" comprising 100.7 L) was collected until start of the main fraction. Following the further processed main fraction, further fractions were collected starting from peak maximum. These fractions ("fractions 2-6"), which comprised different volumes (fraction 2: 1.4 L, fraction 3: 3.7 L, fraction 4: 8.1 L, fraction 5: 3.6 L and fraction 6: 9.7 L), were collected from the descending peak area.

Figure 5:
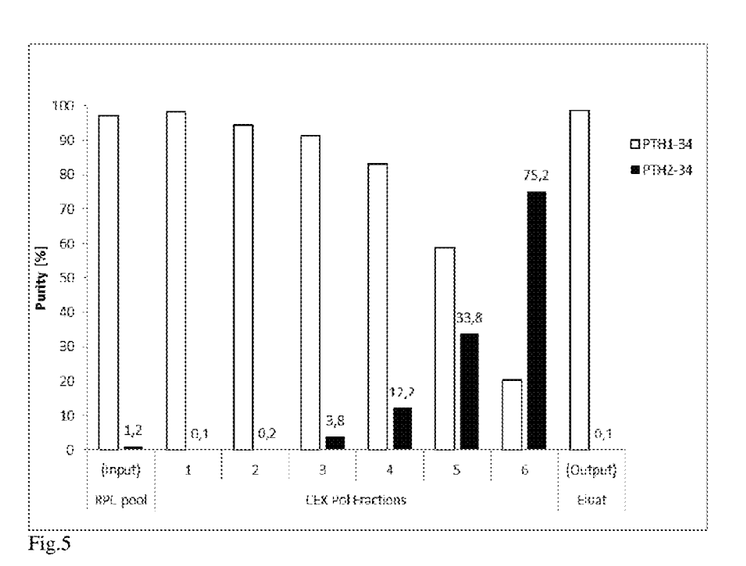
FIG. 5 shows the results of the reversed-phase ultra high performance liquid chromatography (RP-uHPLC) analysis of fractions collected from the cation exchange chromatography run depicted in FIG. 4.

The results of the RP-uHPLC are shown in FIG. 5. It can be seen there that the initial PTH1-34 preparation obtained from RP chromatography contained about 1.2% PTH2-34, while fraction 1 collected after cation exchange chromatography contained only about 0.1% of the truncated polypeptide. Almost the complete PTH2-34 eluted in fractions 3-6, i.e. in the descending peak area. A total of 62.9 g PTH1-34 was loaded to the cation exchange column. The chromatographic process yielded 54.0 g PTH1-34, which represents a recovery of 86%.

From these results, it can therefore be concluded that the method of the present invention is highly effective for separating PTH1-34 from PTH2-34 at preparative scale without any significant loss of PTH1-34. The method is therefore suitable for being used in the large-scale production of PTH1-34.

The invention claimed is:

1. A method for purifying teriparatide by ion exchange chromatography, comprising the steps of
   (a) contacting a fluid which comprises teriparatide with a cation exchange material under conditions that allow for the reversible binding of PTH1-34 to said cation ex-change material;
   (b) optionally washing the cation exchange material to remove unbound material;
   (c) eluting teriparatide by increasing the pH and decreasing the ionic strength,
   wherein said teriparatide comprises or consists of the amino acid sequence of SEQ ID NO:1.

2. The method of claim 1, wherein said PTH1-34 is recombinantly produced teriparatide.

3. The method of claim 1, wherein said cation exchange material comprises one or more of sulfoethyl, sulfopropyl, sulfobutyl or sulfoisobutyl exchanger groups.

4. The method of claim 1, wherein said cation exchange material comprises cross-linked polystyrene-divinylbenzene, polymethacrylate, polyvinyl ether, cellulose, or dextran.

5. The method of claim 1, wherein the eluate obtained in step (c) contains less than 0.5% (w/w) of the fragment PTH2-34.

6. The method of claim 1, wherein binding to said cation exchange material is effected at a pH of between 6.3 and 6.7.

7. The method of claim 1, wherein binding to said cation exchange material is effected in the presence of a binding buffer comprising 10-80 mM Tris.

8. The method of claim 1, wherein binding to said cation exchange material is effected in the presence of a binding buffer comprising 20 mM Tris.

9. The method of claim 7, wherein elution from said cation exchange material is effected in the presence of an eluent comprising 10-80 mM Tris.

10. The method of claim 7, wherein elution from said cation exchange material is effected in the presence of an eluent comprising 20 mM Tris.

11. The method of claim 1, wherein the increase in pH and/or the decrease in ionic strength is effected by using a linear, concave, or convex gradient.

12. The method of claim 1, wherein the increase in pH and/or the decrease in ionic strength is effected by using a stepwise elution.

13. The method of claim 1, wherein said binding buffer has an ionic strength in the range of 1.8 to 3.0 mS/cm.

14. The method of claim 1, wherein said eluent has an ionic strength in the range of 0.2 to 1.2 mS/cm.

15. A method for preparing teriparatide, comprising the steps of
   (a) recombinantly expressing teriparatide in a host cell;
   (b) optionally disrupting the host cells to release the recombinantly expressed teriparatide; and
   (c) purifying the teriparatide by the method of claim 1.

16. The method of claim 15, wherein said host cell is a prokaryotic host cell.

17. The method of claim 15, wherein the method comprises one or more additional chromatography steps prior to or subsequent to step (c).

* * * * *

SEQUENCE LISTING

```
<160> NUMBER OF SEQ ID NOS: 2

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 84
<212> TYPE: PRT
<213> ORGANISM: Homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln
```